United States Patent
Funazaki (10) Patent No.: US 9,291,534 B2
(45) Date of Patent: Mar. 22, 2016

(54) CELL COLLECTION APPARATUS AND CELL COLLECTING METHOD

(71) Applicant: OLYMPUS CORPORATION, Tokyo (JP)

(72) Inventor: Jun Funazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/281,079

(22) Filed: May 19, 2014

(65) Prior Publication Data

US 2014/0255977 A1  Sep. 11, 2014

Related U.S. Application Data (63) Continuation of application No. PCT/JP2012/079988, filed on Nov. 19, 2012.

(30) Foreign Application Priority Data

Nov. 24, 2011 (JP) ................... 2011-256287

(51) Int. Cl.
  *A61B 10/00* (2006.01)
  *G01N 1/31* (2006.01)
  *G01N 1/28* (2006.01)

(52) U.S. Cl.
  CPC ............. *G01N 1/31* (2013.01); *G01N 1/286* (2013.01); *G01N 2001/288* (2013.01); *G01N 2001/2873* (2013.01)

(58) Field of Classification Search
  CPC ................ H01L 21/78; G01N 1/286
  See application file for complete search history.

(56) References Cited

U.S. PATENT DOCUMENTS

| | | | |
|---|---|---|---|
| 3,448,510 A * | 6/1969 | Anderson, Jr. et al. | ......... 29/413 |
| 3,932,220 A | 1/1976 | Liotta | |
| 4,647,543 A | 3/1987 | Stöcker | |
| 4,752,347 A | 6/1988 | Rada | |
| 5,998,129 A | 12/1999 | Schutze et al. | |

(Continued)

FOREIGN PATENT DOCUMENTS

| | | |
|---|---|---|
| EP | 2 579 019 A1 | 4/2013 |
| JP | S48-13260 B1 | 4/1973 |

(Continued)

OTHER PUBLICATIONS

Extended Supplementary European Search Report dated Feb. 5, 2015 from related European Application No. 12 85 0822.3.

(Continued)

*Primary Examiner* — Jyoti Nagpaul

(74) *Attorney, Agent, or Firm* — Scully, Scott, Murphy & Presser, P.C.

(57) ABSTRACT

Provided is a cell collection apparatus includes: a supporter that supports a sheet to which a back surface of a substrate is pasted, the substrate being divided in to plural small pieces with a section of a tissue pasted on a front surface thereof; a needle including needle tips; and a holder that is configured to hold the needle with the needle tips facing the sheet on an opposite side to a substrate side of the sheet, and to move the needle in the forward direction of the needle tips, wherein at least two needle tips are arranged within a region narrower than the back surface of the small piece substantially on the identical plane intersecting with the longitudinal direction of the needle.

8 Claims, 7 Drawing Sheets

(56) References Cited

U.S. PATENT DOCUMENTS

| | | |
|---|---|---|
| 2002/0142412 A1 | 10/2002 | Ogawa et al. |
| 2002/0197770 A1 | 12/2002 | Irie |
| 2003/0032082 A1 | 2/2003 | Leclerc |
| 2004/0014205 A1 | 1/2004 | Banes |
| 2006/0121596 A1 | 6/2006 | Chaumat |
| 2006/0147896 A1 | 7/2006 | Schnetz et al. |
| 2006/0177812 A1 | 8/2006 | Schnetz et al. |
| 2010/0050838 A1 | 3/2010 | Noguchi et al. |
| 2010/0178661 A1 | 7/2010 | Lee et al. |
| 2013/0084599 A1 | 4/2013 | Morimoto |
| 2014/0011233 A1 | 1/2014 | Morimoto |

FOREIGN PATENT DOCUMENTS

| | | |
|---|---|---|
| JP | S55-086173 A | 6/1980 |
| JP | H10-229097 A | 8/1998 |
| JP | 11-148887 A | 6/1999 |
| JP | 11-163006 A | 6/1999 |
| JP | 2000-504824 A | 4/2000 |
| JP | 2002-202229 A | 7/2002 |
| JP | 2002-286592 A | 10/2002 |
| JP | 2003-007652 A | 1/2003 |
| JP | 2003-152056 A | 5/2003 |
| JP | 2003-521685 A | 7/2003 |
| JP | 2004-537712 A | 12/2004 |
| JP | 2005-034058 A | 2/2005 |
| JP | 2006-158394 A | 6/2006 |
| JP | 2008-286528 A | 11/2008 |
| JP | 2009-044123 A | 2/2009 |
| JP | 2009-260226 A | 11/2009 |
| JP | 2010-074135 A | 4/2010 |
| WO | 02/37944 A2 | 5/2002 |
| WO | 2008/053916 A | 5/2008 |
| WO | WO 2013/077337 A1 | 5/2013 |

OTHER PUBLICATIONS

Leica, Microsystems, Leica LMD 7000, p. 2.
International Search Report dated Jan. 29, 2013 issued in PCT/JP2012/079988.
U.S. Office Action dated Jul. 14, 2014 received in related U.S. Appl. No. 13/686,296.
Leica Microsystems, "Leica LMD 6500 Leica LMD 7000, Laser microdissection", p. 2, Jun. 2009, http://www.leica-microsystems.com/fileadmin/downloads/Leica%20LMD7000/Brochures/LMD6500_7000_JP.pdf, together with an English-language translation.

* cited by examiner

CELL COLLECTION APPARATUS AND CELL COLLECTING METHOD

CROSS-REFERENCE TO RELATED APPLICATIONS

This is a continuation of International Application PCT/JP2012/079988, with an international filing date of Nov. 19, 2012, which is hereby incorporated by reference herein in its entirety. This application claims the benefit of Japanese Patent Application No. 2011-256287, filed on Nov. 24, 2011, the content of which is incorporated herein by reference.

TECHNICAL FIELD

The present invention relates to a cell collection apparatus and a cell collecting method.

BACKGROUND ART

Heretofore, the Laser Microdissection (LMD) method has been known as a technique to pick up a micro-region of about several tens microns by cutting it out from a thin tissue section for use in pathological diagnosis and the like (see NPL 1, for example). In the LMD method, the micro-region of the tissue section to be picked up is irradiated with UV laser, by which the micro-region is cut out from the section.

CITATION LIST

Non Patent Literature

{NPL 1}

Leica MICROSYSTEMS, "Leica LMD 6500 Leica LMD 7000", P. 2, [online], [searched on Aug. 30, 2012], Internet <URL:http://www.leicamicrosystems.com/fileadmin/downloads/Leica%20LMD7000/Brochures/LMD6500_7000_JP.pdf>

SUMMARY OF INVENTION

A first aspect of the present invention is a cell collection apparatus including: a supporter that supports a sheet detachably adhering to one end surface of a substrate on whose other end surface a section of a tissue is pasted, the substrate being divided into plural small pieces along a predetermined dividing lines together with the section and allowing at least one of the small pieces to be separated by pressing the one end surface of the small piece; a needle having needle tips configured to pierce the sheet; and a holder that is configured to hold the needle with the needle tips facing the sheet held by the supporter on an opposite side to a substrate side of the sheet, and to move the needle in a forward direction of the needle tips along a longitudinal direction of the needle, wherein at least two needle tips are arranged within a region narrower than the one end surface of the small piece substantially on an identical plane intersecting with the longitudinal direction.

The second aspect of the present invention is a cell collecting method comprising: preparing a substrate that is divided together with a section, which is pasted on one end surface of the substrate, into plural small pieces; pressing the other end surface of the small piece at at least two positions with substantially a same force in strength and direction, thereby separating the small piece; and collecting the separated small piece with a fragment of the section.

DESCRIPTION OF EMBODIMENTS

A cell collection apparatus 1 according to one embodiment of the present invention will be described with reference to drawings, hereinafter.

Figure 1:
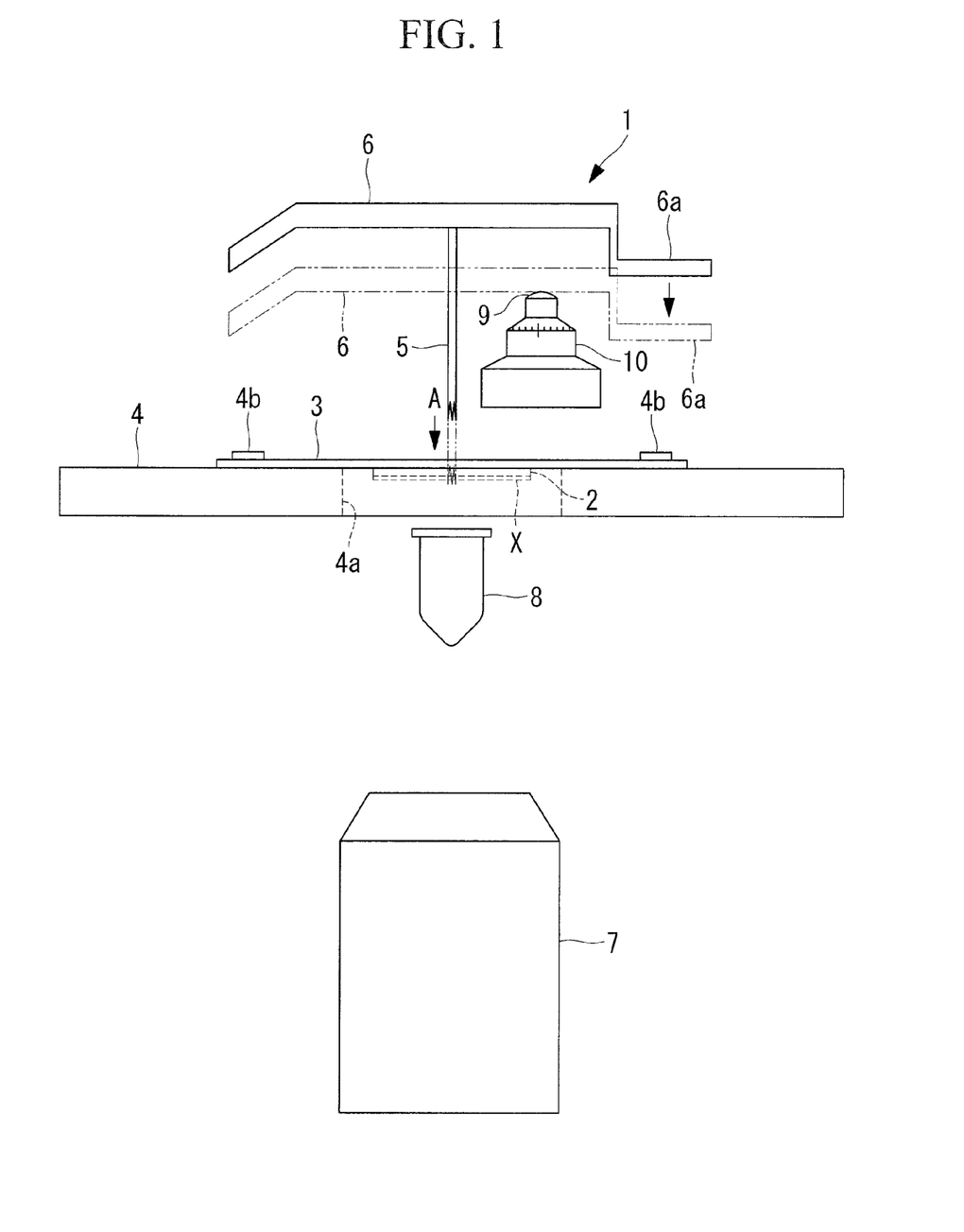
FIG. 1 is a drawing of an overall configuration of a cell collection apparatus according to one embodiment of the present invention.

As shown in FIG. 1, the cell collection apparatus 1 according to the present embodiment includes: a stage (supporter) 4 on which a sheet (sheet) 3, to which a substrate 2 to which a section X of a tissue is pasted adheres, is placed; a needle 5 having four needle tips 5a; and a holder 6 that holds the needle 5 above the stage 4 and that moves the needle 5 in the upward and downward directions.

Figure 2:
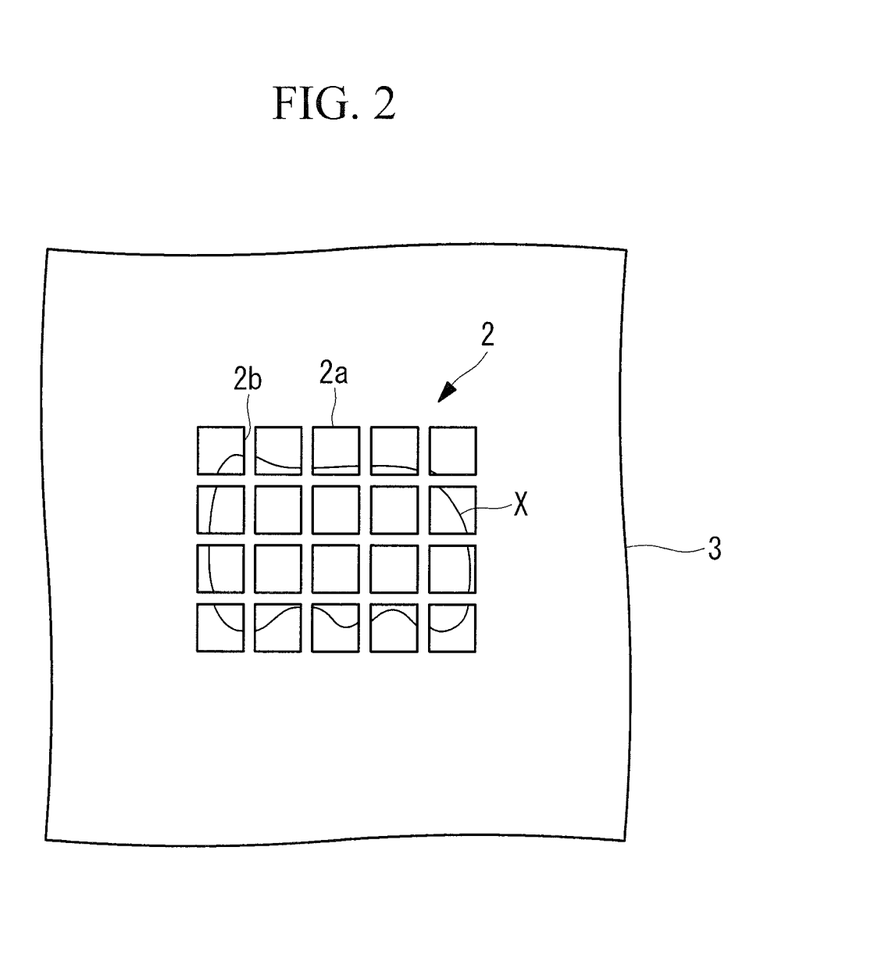
FIG. 2 is a drawing showing an example of a substrate used in the cell collection apparatus of FIG. 1.

As shown in FIG. 2, the section X of a tissue is pasted on a front surface (one end surface) of the substrate 2, and the substrate 2 is divided together with the section X by grooves (dividing lines) 2b into plural small pieces 2a. The back surface (the other end surface) of each small piece 2a detachably adheres to the sheet 3 with adhesive having adequately small adhesiveness. A material transparent to a visible light, such as a glass, may be used in the substrate 2.

Such a substrate 2 may be produced, for example, by bonding a base substrate to which the section X is pasted to the sheet 3 with adhesive, and cutting the base substrate as well the section X on the sheet 3 by use of a scalpel or a glass cutter. Alternatively, a material expandable in the surface direction is used as the sheet 3, the grooves 2b are formed in the base substrate bonded to the sheet 3 using a glass cutter or the like, the base substrate and the section X are divided along the grooves 2d by expanding the sheet 3, and the sheet 3 is held in an expanded state, thereby producing the substrate 2.

In the case of dividing the section X into plural fragments in this manner, the thickness of the section X and the size of the fragment are not limited to specific ones. Hence, a single fragment is allowed to contain sufficiently plenty of cells by producing the section X to be relatively thick, and appropriately adjusting gaps between the grooves 2b.

FIG. 2 shows the substrate 2 formed of the small pieces 2a each having a square end surface and arranged in a square array, but the shape and the arrangement of the small pieces 2a may be appropriately changed. The small pieces 2a may be mutually arranged with their side surfaces in tight contact with one another with no gap thereamong.

The stage 4 is a stage of an inverted microscope having an aperture 4a at its central portion, and movable upward and downward in the vertical direction, and also movable in the horizontal direction. The sheet 3 is placed on the stage 4 such that the surface thereof to which the substrate 2 is pasted faces downward, and the substrate 2 is arranged in the aperture 4a; and the edge of the sheet 3 is pressed with a pressing member 4b such as a clip, thereby stably supporting the sheet 3 on the stage 4 substantially in a horizontal state. The sheet 3 on the stage 4 and the small pieces 2a pasted on the sheet 3 can be observed under high magnification using an objective lens 7 disposed below the stage 4. Space for accepting a collecting container 8 like a micro tube for collecting the small pieces 2a is formed between the stage 4 and the objective lens 7.

Figure 3:
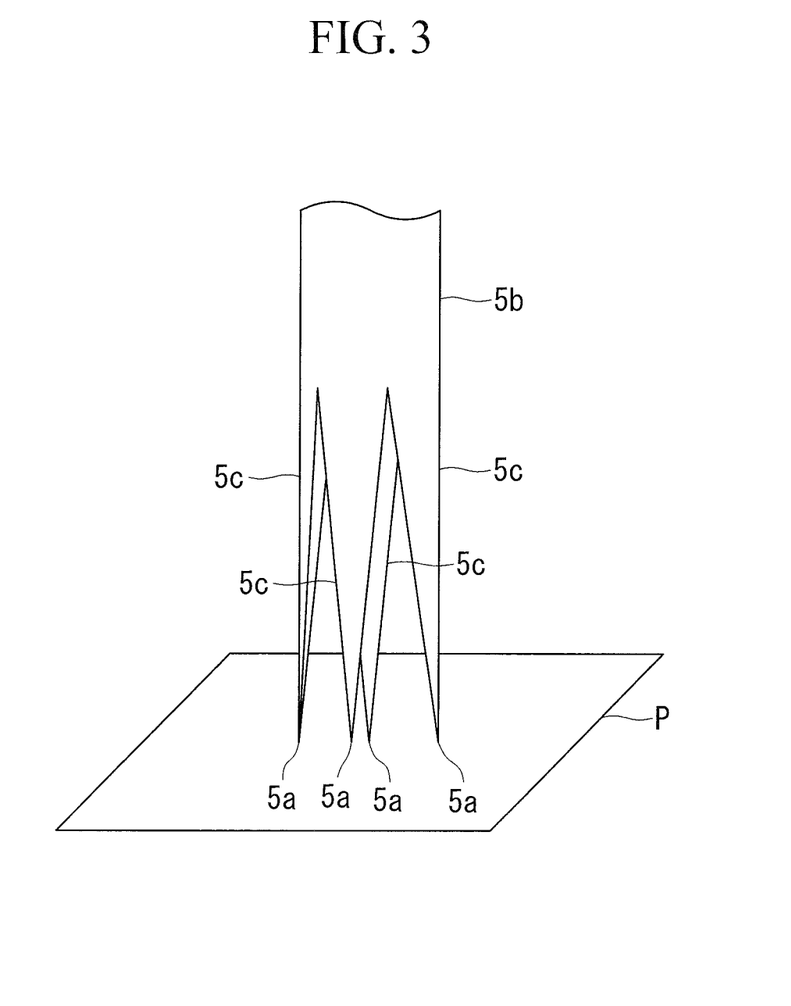
FIG. 3 is a drawing showing needle tips included in the cell collection apparatus of FIG. 1.

The needle 5 includes a single axial portion 5b and a needle portion 5c branching into four pieces on a tip end side of the axial portion 5b. The sharp needle tips 5a that are the tip end of the needle portion 5c are arranged on an identical plane P substantially vertically intersecting with the longitudinal direction of the axial portion 5b.

Figure 4A:
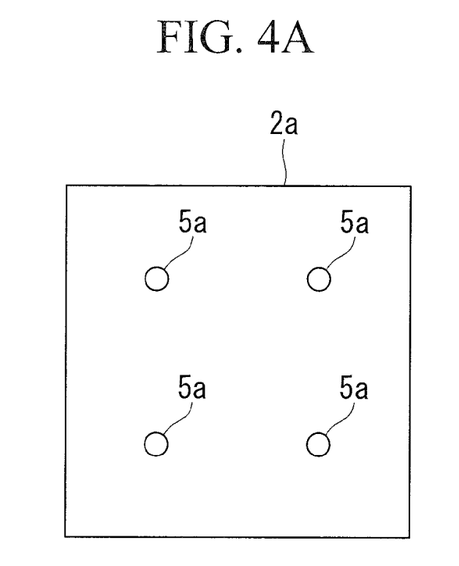
FIG. 4A is a drawing showing a positional relation between a small piece and the needle tips.

The four needle tips 5a are arranged within a narrower region than a back surface of the small piece 2a so that the needle tips 5a can come into contact with the back surface of the single small piece 2a at the same time. The needle tips 5a are arranged to be equivalently distributed to the back surface of the small piece 2a substantially in a square shape. To be specific, the four needle tips 5a are arranged at the positions corresponding to respective apexes of a substantially square shape. The needle 5 is held by the holder 6 in such a manner that the needle tips 5a correspond to respective apexes of the back surface of the small piece 2a (see FIG. 4A), or correspond to substantially each center location of the respective sides of the small piece 2a (see FIG. 4B). Accordingly, when the four needle tips 5a come into contact with the back surface of the small piece 2a, substantially the same pressing force in strength and direction can be applied across the entire back surface thereof.

The holder 6 holds the axial portion 5b of the needle 5 with the needle tips 5a facing downward substantially in the vertical direction. The holder 6 is configured to be movable together with the needle 5 substantially in the vertical direction between a position where the needle tips 5a are located above the sheet 3 placed on the stage 4, and a position where the needle tips 5a piercing the sheet 3 are located below the sheet 3. A layer 6a included in the holder 6 is pressed downward by an operator so that the needle 5 is moved downward substantially in the vertical direction along the longitudinal direction thereof toward the stage 4, as indicated by an arrow A, and the needle tips 5a pierces the sheet 3 substantially in the vertical direction. The holder 6 is also configured to move together with the needle 5 substantially in the horizontal direction.

There is provided a stopper 9 for restricting downward movement of the holder 6 such that projection from the sheet 3 of the needle tips 5a piercing the sheet 3 becomes a predetermined amount. The position in the vertical direction of the stopper 9 is adjustable using a micrometer 10 such that the projection of the needle tips 5a becomes the predetermined amount.

The operation of the cell collection apparatus 1 having the above configuration will be described hereinafter.

In order to collect a fragment in a desired region from the section X of a tissue using the cell collection apparatus 1 according to the present embodiment, the sheet 3 is placed on the stage 4 with the substrate 2 facing downward. The position in the horizontal direction of the stage 4 is adjusted such that the small piece 2a to which the desired fragment of the section X is pasted is arranged substantially at the center of the field of view to be observed through the objective lens 7.

The holder m 6 is moved in the horizontal direction so as to position the four needle tips 5a substantially at the center of the field of view. Then, the collecting container 8 is disposed substantially downward of the vertical direction of the needle tips 5a in space between the stage 4 and the objective lens 7.

Figure 5:
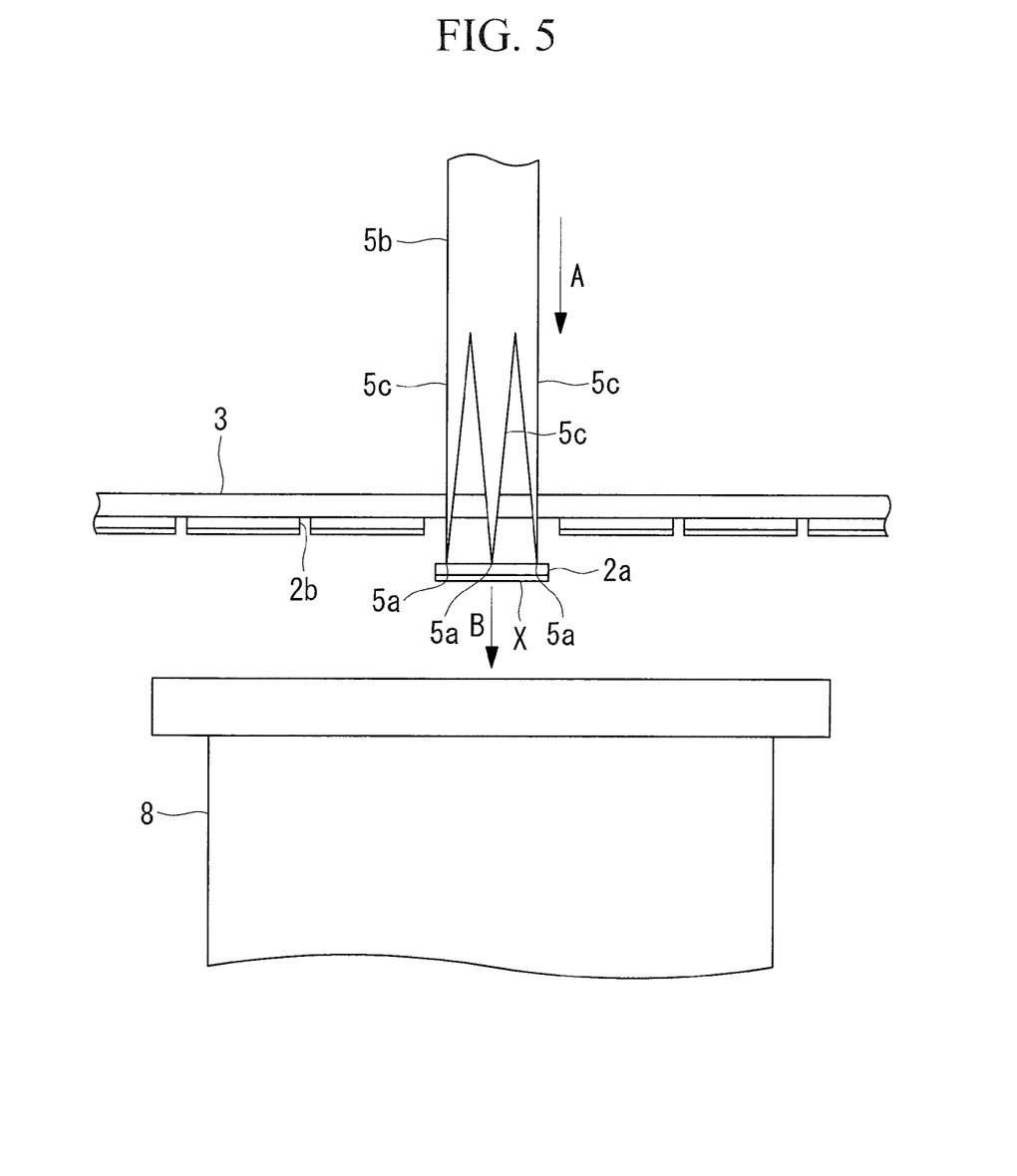
FIG. 5 is a drawing explaining an operation of the cell collection apparatus of FIG. 1.

The layer 6a is pressed and moved down to a position where the layer 6a is locked by the stopper 9 so that the needle 5 is moved in the direction indicated by the arrow A, and the needle tips 5a pierce the sheet 3, as shown in FIG. 5. Through this operation, the back surface of the small piece 2a arranged substantially at the center of the field of view is pressed by the needle tips 5a, and detached from the sheet 3. As indicated by an arrow B, the detached small piece 2a flies toward the collecting container 8 disposed frontward of the moving direction of the needle 5, that is, the pressing direction thereof.

Through the above operation, the desired fragment of the section in a state of adhering to the small piece 2a can be collected in the collecting container 8. In the case of collecting plural fragments from a single section, the needle 5 is moved using the layer 6a until the needle tips 5a reaches the position above the stage 4, and thereafter the same operation may be repetitively carried out.

According to the present embodiment, the desired fragment can be picked up from the section X only with a simple apparatus structure and a simple operation. By pressing the back surface of the small piece 2a with the four needle tips 5a arranged substantially on the identical plane P, the strength and the direction of the pressing force acting on each point of the back surface becomes substantially uniform. Accordingly, it is possible to securely detach the entire back surface of the small piece 2a from the sheet 3, stabilize the flying direction of the small piece 2a in the pressing direction of the needle 5, and securely collect the small piece 2a in the collecting container 8 disposed in advance.

If a relatively large potion on the base end side of the needle tips 5a and the axial portion 5b also pierce the sheet 3 subsequent to the piercing of the needle tips 5a through the sheet 3, through holes formed in the sheet 3 become greater. At this time, it may be considered that neighbor small pieces 2a of the small piece 2a of interest become unexpectedly detached from the sheet 3 when a great impact is applied to the sheet 3, or the through holes are joined together when adjacent small pieces 2a are picked up, and the sheet 3 eventually becomes torn. To the contrary, according to the present embodiment, the configuration of restricting the lower position of the needle tips 5a with the stopper 9 allows only the portion having an adequately small diameter to pierce the sheet 3, thereby maintaining the through holes formed in the sheet 3 to have adequately small diameters, by which the aforementioned inconvenience can be prevented.

Figure 6:
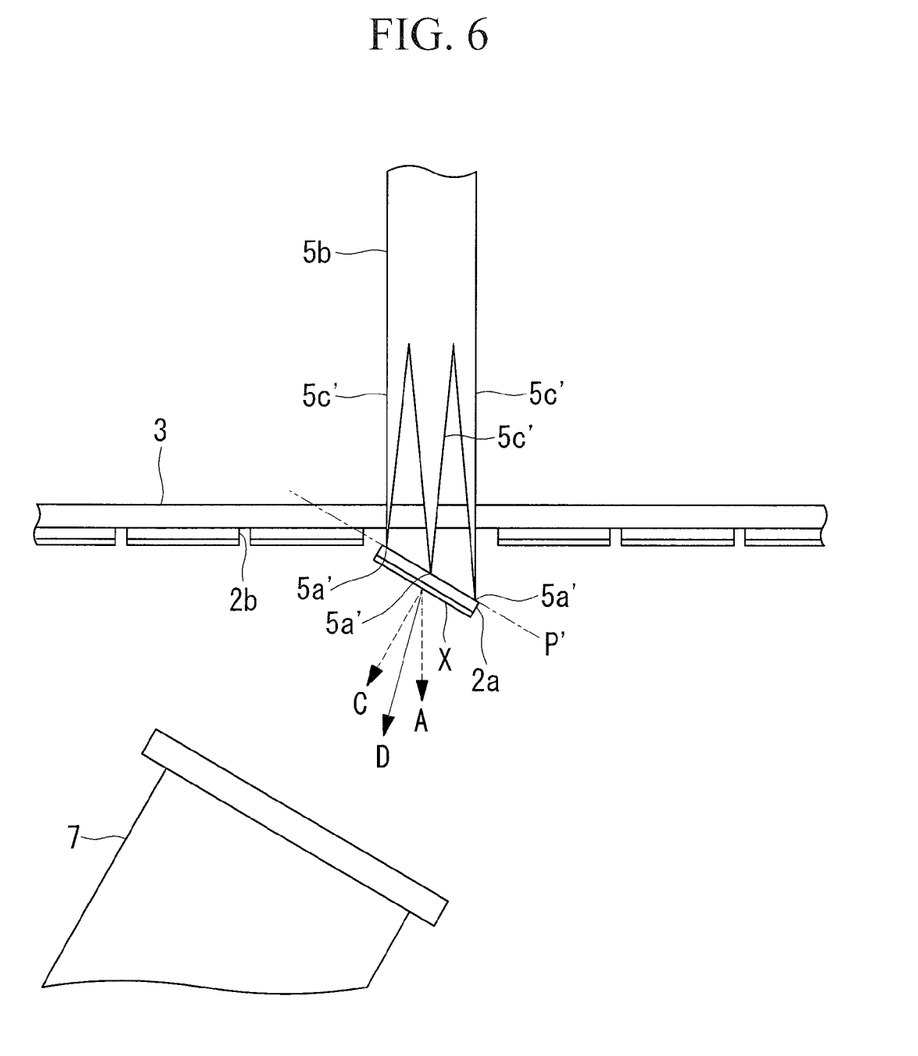
FIG. 6 is a drawing of a partial configuration for explaining a modification of the needle included in the cell collection apparatus of FIG. 1, and the operation of the cell collection apparatus including this needle.

In the present embodiment, it is configured to allow the small piece 2a to fly frontward of the moving direction of the needle 5, but it may be configured to allow the small piece 2a to fly in an oblique direction relative to the moving direction of the needle 5. In this case, the four needle tips 5a' are arranged, as shown in FIG. 6, on the identical plane P' obliquely intersecting with the longitudinal direction of the needle 5. The small piece 2a pressed by the needle tips 5a' flies in a direction indicated by an arrow D obtained by synthetizing the moving direction of the needle 5 indicated by the arrow A and the normal direction of the plane P' indicated by the arrow C, as shown in FIG. 6.

The flying small piece 2a can be securely collected in the collecting container 8, which is disposed in the direction of the arrow D in advance. There exists no collecting container 8 on an optical path between the sheet 3 and the objective lens 7, and thus it is possible to observe the small piece 2a and the needle tips 5a using the objective lens 7 at any time. Accordingly, the process of bringing the needle tips 5a closer to the small piece 2a, and allowing this small piece 2a to fly can be performed while observing this process using the objective lens 7.

In the present embodiment, the needle tips 5a of the needle 5 is configured to have four tips, but the number thereof may be appropriately changed as far as at least two needle tips are arranged on the identical plane intersecting with the longitudinal direction of the needle 5.

In the present embodiment, it is configured to provide the needle 5 including the single axial portion 5b and the four needle portions 5c, and instead of this configuration, it may be configured to arrange plural needles each having a single axial portion, and a single needle portion or plural needle portions in parallel, and to hold these needles with the holder 6.

Figure 7:
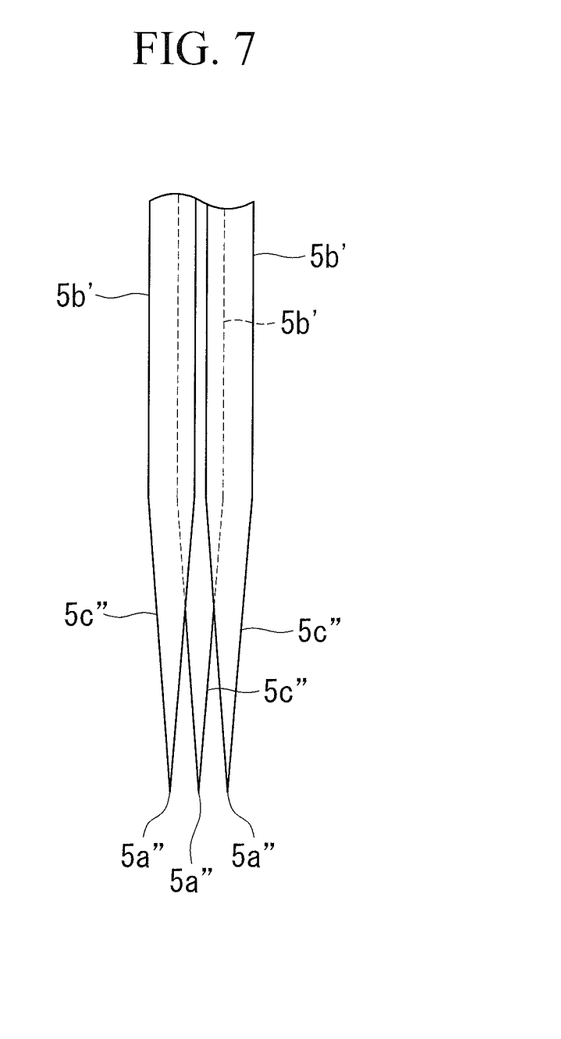
FIG. 7 is a drawing of a partial configuration for explaining another modification of the needle included in the cell collection apparatus of FIG. 1.

FIG. 7 shows a configuration that three needles each having a single axial portion 5b' and a single needle portion 5c" are held in parallel with one another. The three needle tips 5a" are arranged not in the identical straight line, but to define respective apexes of a rectangle. Combination of the plural needles in this manner facilitates change in the number or position of the needle tips 5a".

In the present embodiment, such a configuration has been described that disposes the needle 5 above the substrate 2, and presses the small piece 2a from the top with the needle 5 so as to allow the small piece 2a to fly downward, but the positional relation between the substrate 2 and the needle 5, and the flying direction of the small piece 2a are not limited to this, and may be appropriately changed. For example, the small piece 2a may be pressed from the bottom with the needle 5 so as to allow the small piece 2a to fly in the upward direction. The small piece 2a flying upward may be allowed to adhere to a sticky sheet or the like located above the stage 4, thereby collecting this small piece 2a.

EXAMPLE

Example of the above described embodiment will be described, hereinafter.
1. Production of Substrate One end surface of a cover glass (18 mm×18 mm, thickness of 0.12 mm to 0.17 mm, manufactured by Matsunami Glass Ind., Ltd.) as a base substrate was pasted on a sticky surface of a dicing sheet (UE-111AJ, manufactured by NITTO DENKO CORPORATION) as a sheet, and this cover glass was cut in a grid form using a dicing saw. In this cutting, the cutting margin was set to be 0.08 mm, and the pitch was set to be 0.5 mm. Through this cutting, a small piece array formed of a group of square small pieces each having each side length of 0.42 mm, squarely arranged on the dicing sheet with a pitch of 0.5 mm, was produced as the substrate.

The small piece array was transcribed to another dicing sheet. Specifically, another dicing sheet was pasted to the other end surface of the small piece array, and the dicing sheet on one end surface thereof was detached, by which the small piece array was moved to the other dicing sheet while the arrangement of small piece array was maintained.

This transcription of the small piece array is carried out because the dicing sheet becomes brittle due to the dicing marks formed on the dicing sheet. If the brittleness of the dicing sheet due to the dicing marks cause no influence to the piercing operation using the needle, this transcription is unnecessary. Each side length and the pitch of the small piece are not limited to the above numerical values, and may be appropriately changed depending on the size of the cross section of the section to be cut out, or the like.

The other dicing sheet to which the small piece array was transcribed was expanded by 140% in the surface direction with an expander, and this dicing sheet was held in an expanded state by a grip ring. Subsequently, the dicing sheet was irradiated with ultraviolet rays having a wavelength of 365 nm from the opposite side to the side where the small pieces are pasted of this dicing sheet, thereby sufficiently reducing the adhesiveness of the dicing sheet. Using a UV irradiator (manufactured by OMRON Corporation, body: ZUV-C10, Head: ZUV-H10), Group 1 where ultraviolet-ray irradiation was carried out with an output of approximately 6 mW for 60 seconds, and Group 2 where ultraviolet-ray irradiation was carried out with an output of approximately 130 mW for 20 seconds were prepared. If the dicing sheet originally has a small adhesiveness, the ultraviolet-ray irradiation step may be omitted.
2. Collection of Small Piece The dicing sheet was placed on the stage of the inverted microscope with the surface of the dicing sheet to which the small piece array is pasted facing downward, and the needle tips of the needle were allowed to pierce the dicing sheet from the top at a position corresponding to any of the small pieces in accordance with the same procedure as that in the aforementioned embodiment. Through this operation, the small piece was allowed to be detached from the dicing sheet, and to fly downward to be collected in the micro tube (referred to as a tube, hereinafter) previously disposed 1.3 mm below the lower surface of the dicing sheet.

As the needles, a four-tip needle having four needle tips (Crown Ejector Needle, CN05-32-015-19, manufactured by Micro-Mechanics), and a single-tip needle having a single needle tip (Ejector Needle, SEN-84-07, manufactured by Micro-Mechanics) were used; and the small pieces of Group 1 were picked up using the four-tip needle, and the small pieces of Group 2 were picked up using the single-tip needle.

Figure 4B:
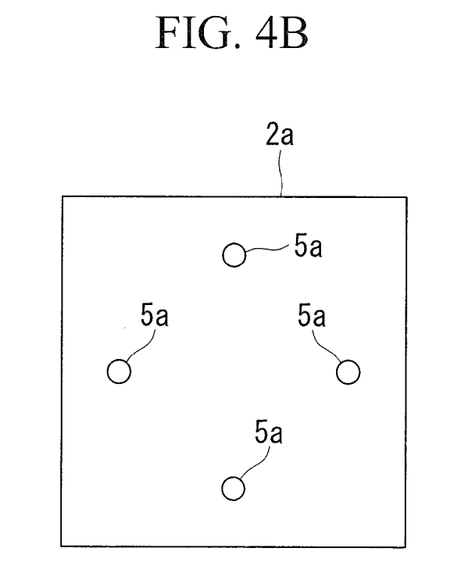
FIG. 4B is a drawing showing the positional relation between the small piece and the needle tips.

Using each needle, pickup of the small pieces was conducted by 100 times within a region of approximately 10 mm×10 mm substantially at the center of the small piece array. The position where the small piece was pressed with the needle tip or tips was substantially the center of the small piece with respect to the single-tip needle, and substantially each center location of respective sides of the small piece with respect to the four-tip needle, as shown in FIG. 4(b). The projection from the dicing sheet of the needle tip or tips piercing the dicing sheet was set to be 1.3 mm. This projection of the needle tip or tips is defined as a projecting amount of only the needle portion piercing the dicing sheet with respect to the four-tip needle, and as a minimum amount required for the needle to pierce the dicing sheet with respect to the single-tip needle.

The result of the pickup of the small pieces conducted in the above manner is shown in Table 1. Phenomena resulting from the pickup of the small pieces may be classified into the following categories: "Collected" representing a case of the small piece of the pickup target collected in the tube; "Remaining" representing a case of the small piece of the pickup target remaining at its original position in the dicing sheet because, for example, its edge portion still adhered to the dicing sheet, or the like; "Re-adhering" representing a case of the small piece of the pickup target once detached from the dicing sheet, but re-adhering to another position in the dicing sheet or to another small piece; "Dropping of Neighbor Small Piece" representing a case of a neighbor small piece of the small piece of the pickup target, which was also detached from the dicing sheet; and "Out of Tube" representing a case of the small piece flying outside the tube. All the cases other than "Collected" show unfavorable results of the small pieces of the pickup target that were not appropriately collected.

TABLE 1

| Pickup result | Single-tip Needle | Four-tip Needle |
| --- | --- | --- |
| Collected | 71% | 100% |
| Remaining | 17% | 0% |
| Re-adhering | 1% | 0% |
| Dropping of Neighbor Small Piece | 9% | 0% |
| Out of Tube | 2% | 0% |

As shown in Table 1, the single-tip needle exhibits high incidence rate of abnormal collection of the small pieces other than "Collected", and the collection rate of the small pieces was 71% at most. Although adjustment of the adhesiveness of the dicing sheet through the ultraviolet-ray irradiation, and the adjustment of the projection of the needle were both carried out, neither the incidence rate of "Remaining" nor the incidence rate of "Dropping of Neighbor Small Piece" could be reduced at the same time. To the contrary, all the small pieces of the pickup target could be normally collected in the tube in the case of using the four-tip needle.

The collection rate of the small pieces in the case of using the four-tip needle is dominantly higher than that in the single-tip needle, and it was confirmed that the present invention can securely collect the small pieces.

In the present Example, no section of a biological tissue was pasted on any small piece, but existence of the section causes no influence to the nature of the present invention directed to the pickup of the small pieces. Accordingly, it is apparent that the same result as Table 1 will be obtained even in the case of pasting the section on the cover glass.

In the present Example, the needle having four tips is used, but it is apparent that the same effect as in the present Example can be attained using any needle having more than two needle tips arranged on the identical plane.

REFERENCE SIGNS LIST

1 Cell collection apparatus
2 Substrate
2a Small piece
2b Groove
3 Sheet (sheet)
4 Stage (supporter)
4a Aperture
4b Pressing member
5 Needle
5a, 5a' Needle tip
5b, 5b' Axial portion
5c, 5c', 5c" Needle portion
6 Holder
6a layer
7 Objective lens
8 Collecting container
9 Stopper
10 Micrometer
X Section

The invention claimed is:
1. A cell collection apparatus comprising:
   a supporter that supports a sheet detachably adhering to one end surface of a substrate on whose other end surface a section of a tissue is pasted, the substrate being divided into plural small pieces along a predetermined dividing lines together with the section and allowing at least one of the small pieces to be separated by pressing the one end surface of the small piece;
   a needle having needle tips configured to pierce the sheet; and
   a holder that is configured to hold the needle with the needle tips facing the sheet held by the supporter on an opposite side to a substrate side of the sheet, and to move the needle in a forward direction of the needle tips along a longitudinal direction of the needle,
   wherein at least two needle tips are arranged within a region narrower than the one end surface of the small piece substantially on an identical plane intersecting with the longitudinal direction.
2. The cell collection apparatus according to claim 1, wherein as many needle tips as apexes of a polygon within the region are arranged at the respective apexes.
3. The cell collection apparatus according to claim 2, wherein the small piece has the one end surface in a polygonal shape, and the needle tips are arranged at respective positions corresponding to substantially each center location of respective sides of the one end surface of the small piece, or to each corner of the small piece.
4. The cell collection apparatus according to claim 1, further comprising a stopper that restricts further forward movement of the needle tips by the holder from a position where projection from the sheet of the needle tips piercing the sheet reaches a predetermined amount.
5. The cell collection apparatus according to claim 1, wherein the needle branches at a middle portion thereof, thereby having at least two needle tips.
6. The cell collection apparatus according to claim 1, wherein the cell collection apparatus comprises plural needles, and the holder holds the plural needles substantially in parallel with one another.
7. The cell collection apparatus according to claim 1, wherein the plane is substantially vertical to the longitudinal direction.
8. The cell collection apparatus according to claim 1, wherein the plane is substantially oblique to the longitudinal direction.

\* \* \* \* \*